United States Patent [19]
Garnier

[11] 3,982,630
[45] Sept. 28, 1976

[54] PACKAGE FOR DENTAL ROOT CANAL AND THE LIKE INSTRUMENTS

[75] Inventor: Marcel Garnier, Besancon, France

[73] Assignee: Micro-Mega S.A., France

[22] Filed: Dec. 6, 1974

[21] Appl. No.: 530,375

[30] Foreign Application Priority Data
Dec. 14, 1973 France ............................. 73.44932

[52] U.S. Cl. .................................. 206/369; 206/72
[51] Int. Cl.² ..................... B65D 85/20; B65D 1/36
[58] Field of Search ............. 206/369, 370, 72, 372

[56] References Cited
UNITED STATES PATENTS
1,292,252  1/1919  Carrier .............................. 206/369
D48,039   10/1915  Niper ............................ 206/72 UX FOREIGN PATENTS OR APPLICATIONS
1,134,613  12/1956  France ............................. 206/369

Primary Examiner—Leonard Summer
Attorney, Agent, or Firm—Robert E. Burns; Emmanuel J. Lobato; Bruce L. Adams

[57] ABSTRACT

A package for dental root canal instruments comprises a rectangular base plate of stamped metal having integral resilient protuberances along a marginal edge defining housings for gripping the handles of the instruments, a part of the handle protruding beyond said marginal edge. A cover with U-section slides is slidably mounted on the base plate to cover the instruments and enclose the protruding handles.

5 Claims, 5 Drawing Figures

FIG. 3
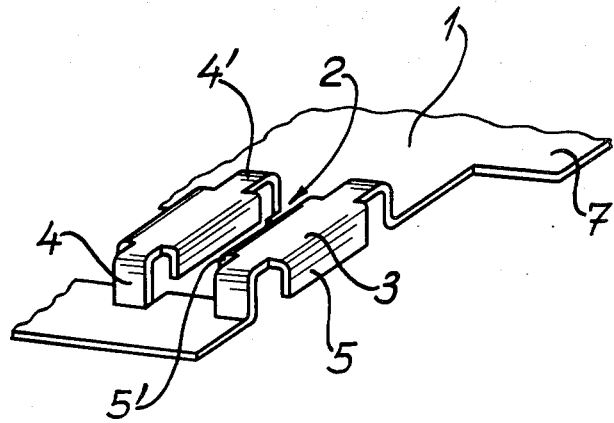
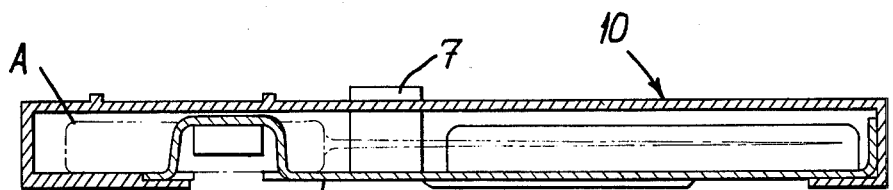
FIG. 5
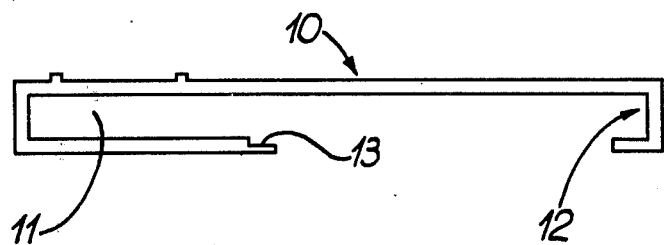
FIG. 4

PACKAGE FOR DENTAL ROOT CANAL AND THE LIKE INSTRUMENTS

BACKGROUND OF THE INVENTION

The invention concerns packages for holding and storing dental root canal instruments provided with a handle, such as nerve broaches.

Dental root canal instruments such as nerve broaches are fragile and difficult to handle. For this reason it has already been proposed to store them in easily pilable and transportable packages. To date, these packages, manufactured of plastic material or of metal, have included parallel grooves or housings in which the instruments were placed and held by a protective cover. This type of package however involves several drawbacks. On the one hand, the access to the instruments by the practitioner's fingers is difficult because of the narrowness of the grooves or housings in which the instruments are placed, and on the other hand the instruments are generally held in place in the grooves or housings by the cover; once the cover is removed, there is thus a risk of them falling out and consequently becoming damaged. Some known packages have been fitted with spring clips for gripping the instrument handles to avoid the last mentioned drawback, but this has involved a complication in assembly and does nothing to avoid the first mentioned drawback.

SUMMARY OF THE INVENTION

The present invention proposes to remedy these drawbacks by providing a package for dental root canal instruments in which the instruments are firmly held and are easily accessible.

According to the invention, there is provided a package for holding in spaced-apart relationship from one another dental root canal and the like instruments such as nerve broaches each including a narrow elongate shank extending from an enlarged handle, comprising a base plate including towards a marginal edge thereof a plurality of protuberances integral with and protruding from one face of the base plate and being spaced-apart along the general direction of said edge, adjacent pairs of said protuberances facing one another to define means for gripping the handle of an instrument disposed transverse to said edge with an end part of the handle opposite the shank protruding from the base plate beyond said edge, and a cover movable from a position mounted on the base plate covering the shanks and enclosing the handles of instruments held on the base plate to a position uncovering the instruments and allowing access to said protruding ends of the handles.

BRIEF DESCRIPTION OF THE DRAWINGS

An embodiment of the invention will now be further described, by way of example, with reference to the accompanying drawings, in which:

FIG. 3 is a perspective view of part of the base plate;

FIG. 4 is a side-view of a protective cover which can be slid on the base plate, and;

FIG. 5 is a cross-sectional view of the base plate and the protective cover mounted on the base plate.

DESCRIPTION OF THE PREFERRED EMBODIMENT

Figures 1, 2:
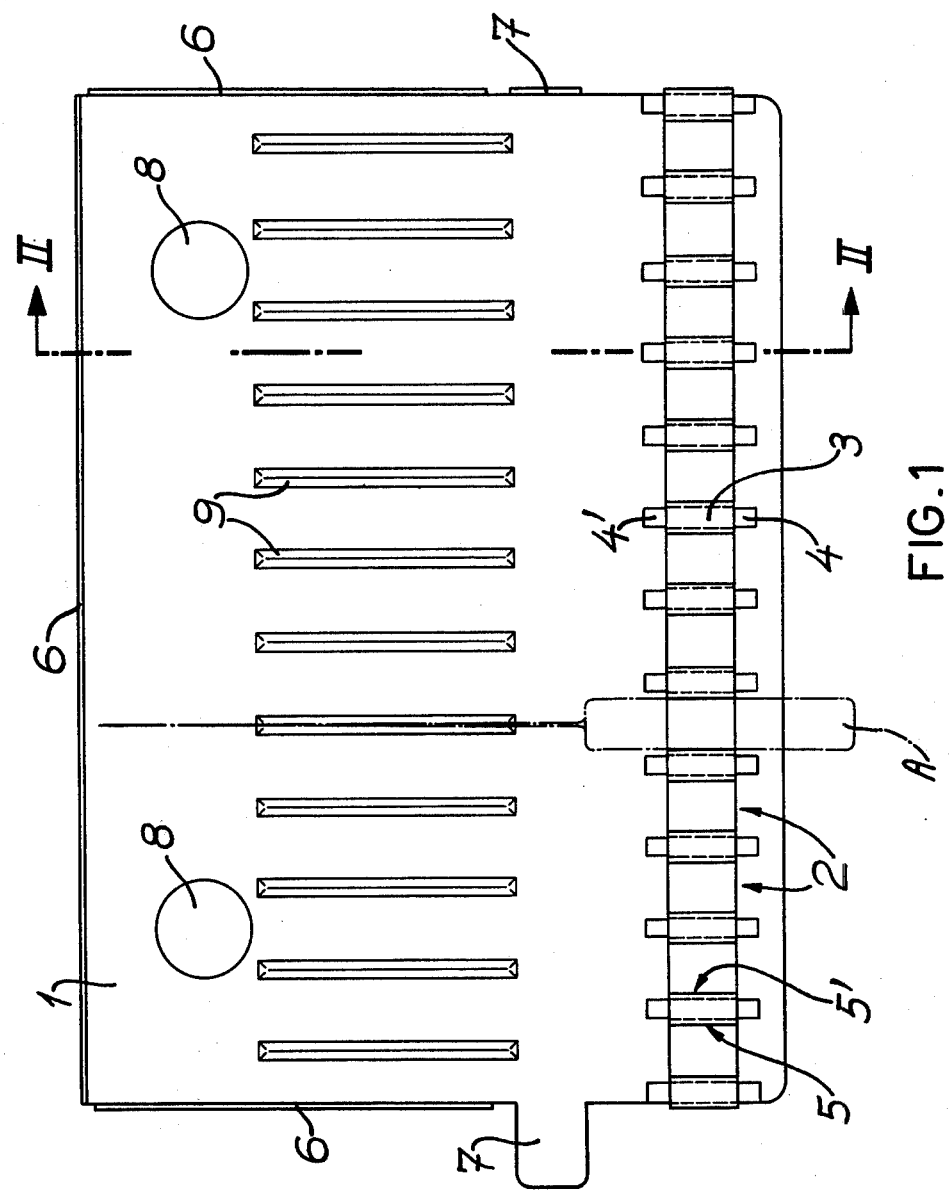
FIG. 1 is a plan view of a base plate of a package.
FIG. 2 is a cross-section taken along line II—II of FIG. 1.

The package comprises a generally rectangular base plate or bottom 1 formed by a stamped thin sheet of metal, along a marginal edge of which are formed several parallel housings 2 to receive the handles of root canal instruments A. These housings 2 are defined by bridges 3 cut out of and protruding from the bottom, and formed by stamping. The central zone of each bridge 3 is wider than its end parts 4, 4' which attach it to the main part and the marginal edge part of the bottom 1, and the protruding edges 5, 5' of this central zone are bent downwardly by 90° and form lateral walls defining the housings 2. In this manner, these lateral walls 5, 5' have a certain resilience and the handle of an instrument A may thus be resiliently held between the facing walls of two adjacent bridges.

The metallic bottom 1 also has on its three other edges upturned flanges 6 and its lateral sides are each provided with a foldable tab 7 serving to secure a protective cover 10, FIG. 4. Handling holes 8 are provided in the bottom 1 to facilitate positioning thereof during the different phases of its manufacture, and parallel grooves 9 are provided to delineate the positions of the shanks of the instruments held in the package.

A root canal instrument A is shown (FIG. 1) placed in the housing 2, with its handle forced between the lateral walls 5, 5' of two adjacent bridges 3, with an end part of the handle, opposite to the shank, protruding from the marginal edge of bottom 1, which facilitates gripping thereof.

A protective cover 10 (FIG. 4) is slidably mounted on the bottom 1 as shown in FIG. 5. This cover 10 includes longitudinal edges of generally U-section forming a first deep U-section slide 11 corresponding to said marginal edge of the bottom 1 adjacent housings 2, and a second shallow slide 12 corresponding to the opposite edge of the bottom 1. A longitudinal groove 13 is formed along the inner face of the edge of the first slide 11 and fits against said marginal edge of bottom 1. The slide 12 engages about flange 6 on the opposite edge of bottom 1 and under the main body of bottom 1. The cover 10 is preferably manufactured from a transparent material, for example a plastic material and thus enables the stored instruments to be seen.

When the cover 10 is in its closed position, held by the upstanding tabs 7, as shown in FIG. 5 it covers the instruments A and the U-section slide 11 encloses the handles of the instrument A which protrude beyond said marginal edge of the bottom 1. The cover 10 can be slid by folding down one of the tabs 7 to uncover the instruments A and allow access to the protruding ends of the instrument handles.

The described package has several advantages, in particular the resilience of the lateral walls 5, 5' of the protuberances formed by bridges 3 enables handles of slightly different diameters to be held, the flexibility of these lateral walls compensating for such differences. Also, because the bottom 1 is metallic it is possible to place it with held instruments in a sterilizer once the protective cover 10 has been removed. The instruments are thus better protected than if they were disposed at random during sterilization.

What is claimed is:

1. A package holding in spaced-apart relationship from one another dental instruments of the type having a narrow elongate shank extending axially from an elongate handle, comprising; a base plate comprised of a main part, a marginal edge part adjacent thereto, and a plurality of protuberances integral with said main part and said marginal edge part of the base plate and being spaced apart along the general direction of said edge part, said protuberances being formed by generally parallel protruding bridges each including respective narrow end portions attached to said main part and said marginal edge part, and a widened central part having edges folded down toward said base plate to form resilient side walls, adjacent pairs of said protuberances disposed with their respective resilient side walls facing one another to define means for gripping the handle of an instrument disposed transverse to said edge part with an end part of the instrument handle opposite the shank protruding from the base plate beyond said edge part, and a cover movable from a position mounted on the base plate covering the shanks and enclosing the handles of the instruments held on the base plate to a position uncovering the instruments and allowing access to said protruding ends of the handles.

2. A package according to claim 1, in which the base plate is rectangular and the cover includes opposed edges with facing U-sections which slidably engage said marginal edge and the opposite edge of the base plate.

3. A package according to claim 2, in which the U-section engaging said marginal edge is deeper than that engaging the opposite edge of the plate and has on the inner face of its edge a longitudinal groove which fits against said marginal edge, said opposite edge of the base plate being upturned and the corresponding U-section of the cover engaging about said upturned edge and under the main body of the base plate.

4. A package for dental instruments, comprising: a base plate comprised of a main part, a marginal edge part adjacent thereto, and a plurality of protuberances integral with said main part and said marginal edge part of said base plate and spaced apart along the general direction of said marginal edge part; said protuberances being formed by generally parallel protruding bridges each including respective narrow end portions attached to said main part and said marginal edge part, and a widened central part having edges folded down toward said base plate to form resilient side walls, adjacent pairs of said protuberances disposed with their respective resilient side walls facing one another to define means for gripping an instrument handle therebetween; and a cover movable from a position mounted on and covering the base plate to a position uncovering the base plate.

5. A package according to claim 4, wherein said base plate is rectangular, and wherein said cover includes a first U-shaped edge portion for engaging said marginal edge part of said base plate and having an inner face with a grooved edge for receiving said marginal edge part, and a second U-shaped edge portion opposite said first U-shaped edge portion for engaging an edge of said main part of said base plate opposite said marginal edge part.

* * * * *